(12) United States Patent
Wales et al.

(10) Patent No.: US 11,197,664 B2
(45) Date of Patent: *Dec. 14, 2021

(54) SYSTEM AND METHOD FOR SECURING AN IMPLANT TO TISSUE

(71) Applicant: Boston Scientific Neuromodulation Corporation, Valencia, CA (US)

(72) Inventors: Lawrence W. Wales, Maplewood, MN (US); Jeffrey J. Peters, Excelsior, MN (US); Vic Fabano, Minneapolis, MN (US); Ishmael Bentley, Eagan, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 16/377,776

(22) Filed: Apr. 8, 2019

(65) Prior Publication Data

US 2019/0231341 A1   Aug. 1, 2019

Related U.S. Application Data

(63) Continuation of application No. 15/383,749, filed on Dec. 19, 2016, now Pat. No. 10,299,783, which is a
(Continued)

(51) Int. Cl.
*A61B 17/04* (2006.01)
*A61M 25/04* (2006.01)
(Continued)

(52) U.S. Cl.
CPC ...... *A61B 17/0401* (2013.01); *A61B 17/0469* (2013.01); *A61B 17/06166* (2013.01);
(Continued)

(58) Field of Classification Search
CPC ............. A61B 17/04; A61B 17/0401; A61B 17/0469; A61B 17/06166;
(Continued)

(56) References Cited

U.S. PATENT DOCUMENTS

| 5,269,809 A | 12/1993 | Hayhurst et al. |
| 5,370,662 A | 12/1994 | Stone et al. |

(Continued)

FOREIGN PATENT DOCUMENTS

WO   2012/151356 A1   11/2012

OTHER PUBLICATIONS

International Search Report and Written Opinion for PCT/US2013/029413 dated Jun. 20, 2013.
(Continued)

*Primary Examiner* — Vi X Nguyen
(74) *Attorney, Agent, or Firm* — Branch Partners PLLC; Bruce E. Black

(57) ABSTRACT

A system and method for securing a medical implant within a patient includes disposing an anchor element around the implant, the anchor element including a pair of tabs each including an eyelet, and a flexible intermediate portion between the tabs, by positioning the implant within the intermediate portion and folding the anchor element such that the tabs contact one another. The anchor element is positioned at a desired implantation position with the tabs proximate soft tissue of the patient. The method further includes inserting a distal tip of a fixation element delivery tool through the eyelets and into the soft tissue, the fixation element including at least one tissue anchor and an adjustable suture arrangement coupled to the tissue anchor. The tissue anchor is deployed from the delivery tool and into the soft tissue of the patient. The delivery tool is withdrawn and the adjustable suture arrangement is tightened.

20 Claims, 9 Drawing Sheets

Related U.S. Application Data continuation of application No. 14/569,505, filed on Dec. 12, 2014, now Pat. No. 9,554,791, which is a continuation of application No. 13/787,432, filed on Mar. 6, 2013, now Pat. No. 8,936,622.

(60) Provisional application No. 61/607,636, filed on Mar. 7, 2012.

(51) Int. Cl.
*A61B 17/06* (2006.01)
*A61N 1/05* (2006.01)

(52) U.S. Cl.
CPC ............. *A61M 25/04* (2013.01); *A61N 1/057* (2013.01); *A61B 2017/0406* (2013.01); *A61B 2017/0409* (2013.01); *A61B 2017/0414* (2013.01); *A61B 2017/0464* (2013.01); *A61B 2017/0496* (2013.01); *A61B 2017/06052* (2013.01); *A61B 2017/06176* (2013.01); *A61N 2001/058* (2013.01); *A61N 2001/0582* (2013.01)

(58) Field of Classification Search
CPC .... A61B 2017/0652; A61B 2017/0409; A61B 2017/0414; A61B 2017/0406; A61B 2017/0464; A61B 2017/0496; A61B 2017/06176; A61B 17/06; A61B 2017/06052; A61N 1/057; A61N 2001/058; A61N 2001/0582
See application file for complete search history.

(56) References Cited

U.S. PATENT DOCUMENTS

| | | | |
|---|---|---|---|
| 6,589,279 | B1 | 7/2003 | Anderson et al. |
| 8,936,622 | B2 | 1/2015 | Wales et al. |
| 9,554,791 | B2 * | 1/2017 | Wales ................. A61B 17/0469 |
| 10,299,783 | B2 * | 5/2019 | Wales ................... A61M 25/04 |
| 2003/0014117 | A1 * | 1/2003 | Lambrecht .............. A61F 2/441 |
| | | | 623/17.16 |
| 2006/0235484 | A1 | 10/2006 | Jaax et al. |
| 2006/0264948 | A1 | 11/2006 | Williams |
| 2007/0010794 | A1 | 1/2007 | Dann et al. |
| 2007/0050005 | A1 | 3/2007 | Lauro |
| 2007/0100348 | A1 | 5/2007 | Cauthen et al. |
| 2007/0233064 | A1 | 10/2007 | Holt |
| 2008/0275401 | A1 | 11/2008 | Sage et al. |
| 2009/0248095 | A1 | 10/2009 | Schleicher et al. |
| 2009/0259260 | A1 | 10/2009 | Bentley et al. |
| 2010/0094425 | A1 * | 4/2010 | Bentley .............. A61B 17/0482 |
| | | | 623/17.16 |
| 2012/0330355 | A1 | 12/2012 | Finley et al. |

OTHER PUBLICATIONS

Official Communication for U.S. Appl. No. 14/569,505 dated Jun. 15, 2016.

Official Communication for U.S. Appl. No. 15/383,749 dated Oct. 5, 2018.

\* cited by examiner

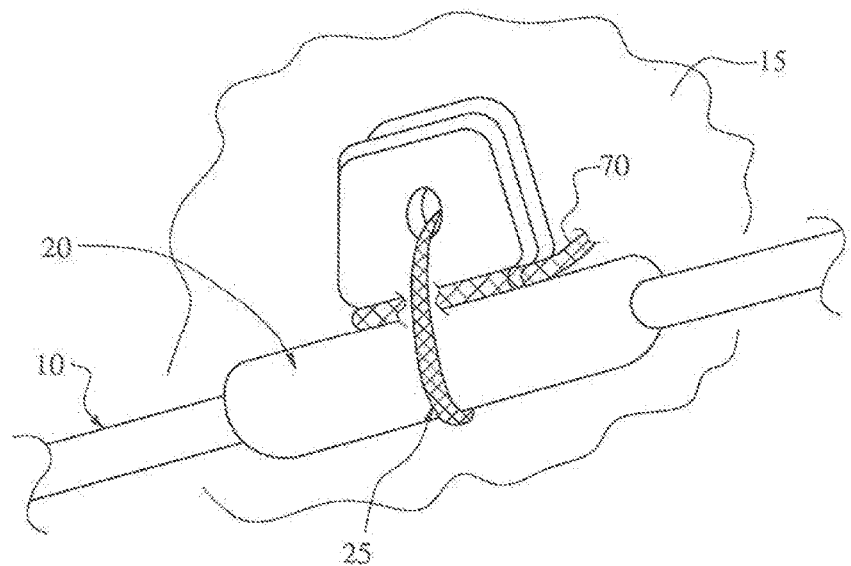
FIG. 1
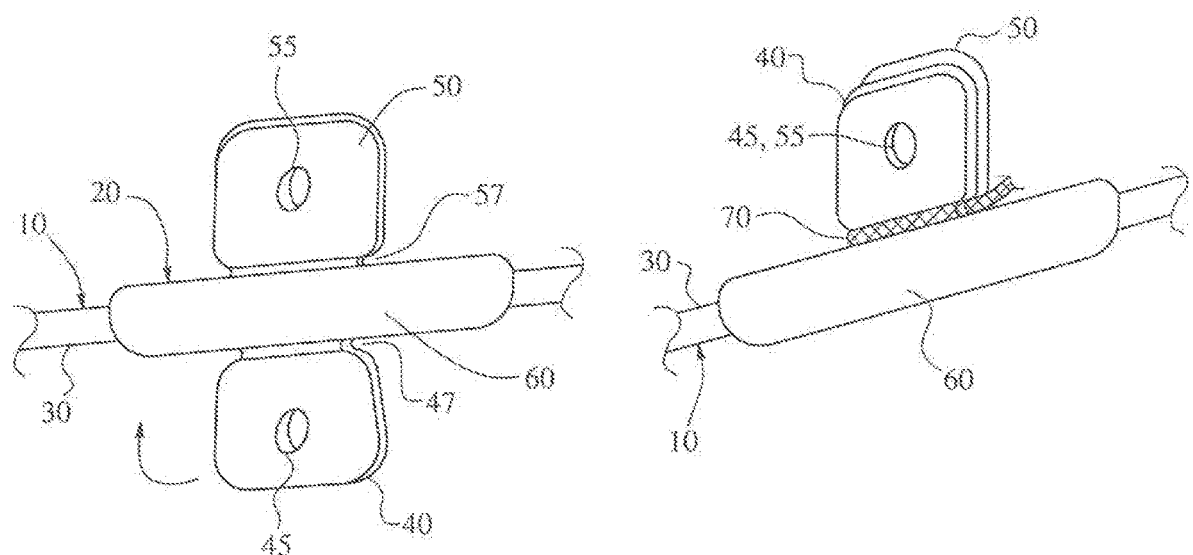
FIG. 2
FIG. 3

SYSTEM AND METHOD FOR SECURING AN IMPLANT TO TISSUE

CROSS-REFERENCE TO RELATED APPLICATIONS

This application is a continuation of U.S. patent application Ser. No. 15/383,749 filed Dec. 19, 2016 which is a continuation of U.S. patent application Ser. No. 14/569,505 filed Dec. 12, 2014, which issued as U.S. Pat. No. 9,554,791, which is a continuation of U.S. patent application Ser. No. 13/787,432 filed Mar. 6, 2013, which issued as U.S. Pat. No. 8,936,622, which claims the benefit under 35 U.S.C. § 119(e) of U.S. Provisional Patent Application Ser. No. 61/607,636 filed on Mar. 7, 2012, all of which are incorporated herein by reference.

TECHNICAL FIELD

The present invention relates to devices and methods for anchoring implants within a patient's body. More specifically, the invention relates to methods for anchoring elongated implants to tissue using an implantable suture assembly and associated delivery tools.

BACKGROUND

Conventional techniques for anchoring elongated implants, e.g., implantable catheters for use in pain management systems such as stimulators, drug pumps and deep brain stimulation (DBS) systems require manually tying one or more sutures to engage the elongated implant to the patient's soft tissues. There is a need for improved anchoring techniques for such devices.

SUMMARY

In one embodiment, the present invention is a system and method for securing a medical implant within a patient. The method comprises disposing an anchor element around the implant, the anchor element includes a pair of tabs, each including an eyelet, and a flexible intermediate portion between the tabs, wherein disposing the anchor element around the implant includes positioning the implant within the intermediate portion and folding the anchor element such that the tabs contact one another and the eyelets align. The anchor element is positioned at a desired implantation position with the tabs positioned proximate soft tissue of the patient. The method further comprises inserting a distal tip of a fixation element delivery tool through the eyelets and into the soft tissue, the fixation element including at least one tissue anchor and an adjustable suture arrangement coupled to the tissue anchor. The at least one tissue anchor is deployed from the delivery tool and into the soft tissue of the patient. The delivery tool is withdrawn from the soft tissue and the eyelets of the anchor element, and the adjustable suture arrangement is tightened to secure the anchor element against the soft tissue. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a schematic illustration showing an elongated medical implant secured to soft tissue using a fixation element and anchor element according to one embodiment of the present invention.

FIGS. 2 and 3 are perspective views of the medical implant and anchor element of FIG. 1 prior to implantation according to one embodiment.

Figure 4:
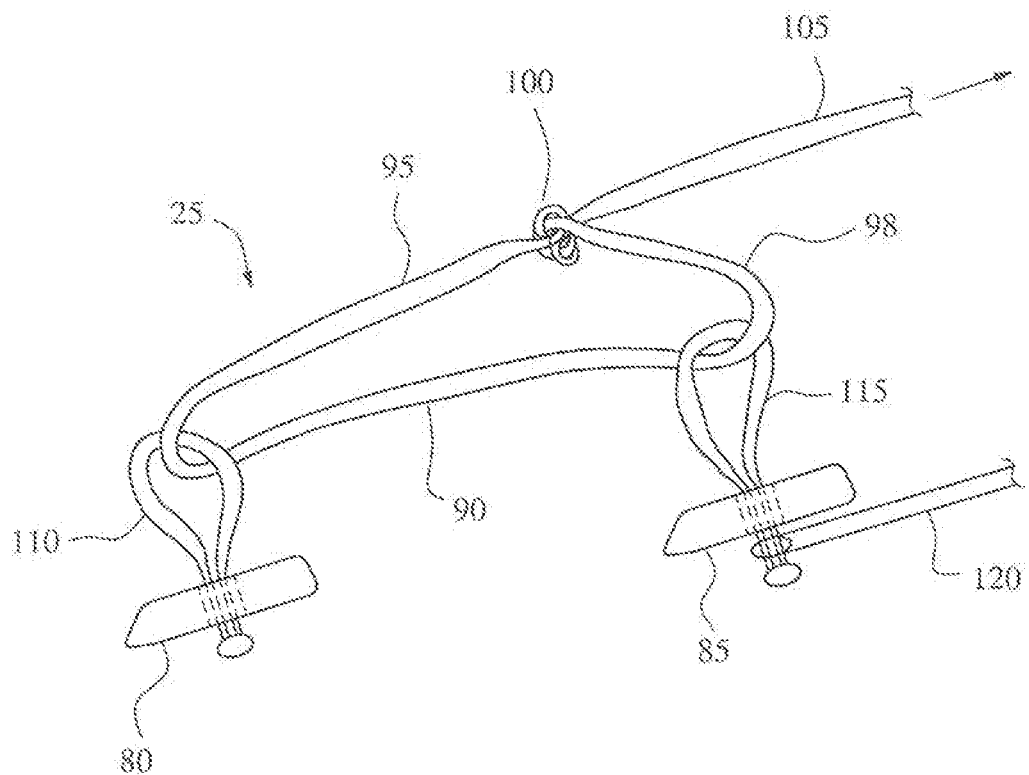
FIG. 4 is a schematic illustration of a fixation element for use in securing the medical implant and anchor element of FIG. 1 to tissue according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration showing an elongated medical implant 10 secured to soft tissue 15 using an anchor element 20 and a fixation element 25 according to one embodiment of the present invention. As shown in FIG. 1, the implant 10 has a flexible, elongated body. In various embodiments, the implant 10 can be any conventional implantable device for use in, for example pain management systems such as stimulators, drug pumps and deep brain stimulation (DBS) systems. As is known in the art, such implant can be in the form of electrode leads or catheters coupled to an implanted therapy device (not shown) such as a stimulator or drug pump. The particular type of therapy device employed is not critical to the various embodiments of the present invention.

The implant 10 is secured in a desired implantation position by the anchor element 20 and the fixation element 25. In the illustrated embodiment, the anchor element 20 is coupled to and frictionally engages the implant 10, and the fixation element 25 is securely coupled to the anchor element 20 and the soft tissue 15, thereby securing the implant 10 in place to inhibit movement of the anchor element 20 and the implant 10 at the fixation site. The particular fixation site, and in turn, the particular soft tissues to which the implant 10, the anchor element 20 and the fixation element 25 will be secured, depends on the particular type of therapy being delivered. For example, stimulators for pain management can be used to directly stimulate the spinal cord or spinal nerves, and thus the implants 10 used therewith will be secured to tissue adjacent the patient's vertebral column. Similarly, pain pumps and the associated implants 10 may also be implanted near the vertebral column and secured to similar tissues, e.g., connective tissue or fascia. The anchor elements 20 and the fixation elements 25 discussed herein are adapted for use in connection with a variety of implantation locations and tissue types.

FIGS. 2 and 3 are perspective views of the medical implant 10 and the anchor element 20 prior to implantation according to one embodiment. As shown, the implant 10 has a flexible, elongated body 30 made of a biocompatible material. In various embodiments, the implant 10 may include an internal lumen (not shown) for conveying a payload (e.g., drug) and/or to assist in delivery by receiving a stylet, guidewire or similar delivery instrument. In addition or in lieu of an internal lumen, depending on the type of implant 10 and therapy device being employed, the implant 10 may include internal conductor wires (also not shown) to couple the therapy device to other structures, e.g., electrodes (not shown), on the implant 10. In various embodiments, the implant body 30 of the implant 10 may be made of a biocompatible elastomeric or polymeric material, e.g., silicone rubber, polyurethane and the like.

In the illustrated embodiment, the anchor element 20 includes a tab 40 having an eyelet 45 and a suture notch 47, an opposite tab 50 having an eyelet 55 and a suture notch 57, and an intermediate portion 60 between the tabs 40, 50. As shown, the anchor element 20 is configured so that the implant 10 can be received within the intermediate portion 60 of the anchor element 10. Thus, the intermediate portion 60 is configured as a generally tubular sleeve sized to receive the implant 10. In one embodiment, the intermediate portion 60 can be configured with a side-opening slit through which the implant 10 can be laterally inserted, after which the intermediate portion 60 partially or completely closes about the implant 10. In another embodiment, the intermediate portion 60 can be a continuous tubular sleeve, such that the implant 10 can be longitudinally inserted into the sleeve to occupy the position shown in FIG. 2 disposed about the body 30 of the implant 10.

In the illustrated embodiment, anchor element 20 is a wing-type anchor, in that tabs 40, 50 extend laterally like wings with respect to the intermediate portion 60. In the various embodiments, the anchor element 20 is sufficiently flexible such that the tabs 40, 50 can be folded toward one another until they are in abutment with one another. This configuration is shown in FIG. 3. As shown, in this folded configuration, the eyelets 45, 55 are aligned with one another so that they can receive the fixation element 25, as shown and explained in further detail below. As further shown, in the illustrated embodiment, a suture loop 70 is disposed about the tabs 40, 50 within the notches 47, 57, which operates to retain the anchor element 20 in the folded configuration shown in FIG. 3. In various embodiments, folding the anchor element 20 as shown in FIG. 3 tends to cause the intermediate portion 60 to radially compress the implant body 30, thus increasing frictional engagement between the intermediate portion 60 and the implant body 30. This engagement serves to enhance the anchoring function of the anchor element 20.

In various other embodiments of the invention, however, the anchor element 20 is not folded over. Rather, the anchor element 20 can remain in its unfolded state as shown in FIG. 2 and the anchor element and implant 10 can be secured to the soft tissue 15 using two fixation elements 25 each corresponding to one of the eyelets 45, 55, or alternatively, a single fixation element 25 including portions inserted through each of the eyelets 45, 55.

In various embodiments, the anchor element 20 can be made from any variety of relatively pliable biocompatible materials. In various embodiments, such materials can include silicone rubber, polyurethane, or similar polymers. In various embodiments, the intermediate portion 60 can include surface features or treatments (e.g., roughening, bumps, ridges, and the like) to enhance frictional engagement with the body 30 of the implant 10.

FIG. 4 is a schematic illustration of a fixation element 25 according to one embodiment. As shown, the fixation element 25 includes a pair of tissue anchors 80, 85 and an adjustable suture arrangement 90 coupled to the tissue anchors 80, 85. In the illustrated embodiment, the suture arrangement 90 includes a primary suture element 95 forming an adjustable suture loop 98 including a knot 100 and a tether 105 allowing the suture loop to be tightened to reduce the size of the suture loop 98.

As further shown, the suture arrangement 90 includes connecting sutures 110, 115 coupling the tissue anchors 80, 85, respectively, to the primary suture element 95 within the suture loop 98. In the illustrated embodiment, the connecting sutures 110, 115 are formed as suture loops through which the primary suture element 95 extends and connected, respectively, to the tissue anchors 80, 85. This configuration of the connecting sutures 110, 115 allows them to slide along the primary suture element 95 as the suture loop 98 is tightened. In the illustrated embodiment, the suture arrangement 98 also includes a safety line 120 fixedly connected to the connecting suture 115. In some embodiments, the safety line 120 is omitted.

In general, the suture arrangement 90 can be configured and used in substantially the same or an identical manner as any of the suture and anchor assemblies illustrated in FIGS. 7A-7C, 8A-8C, 9 and 33A-33D and described in the corresponding text of commonly-assigned U.S. Patent Application Publication 2007/0100348. In addition, the suture arrangement 90 can be delivered using a fixation element delivery tool such as, for example, the fixation delivery apparatus illustrated in FIGS. 33A-33D of the aforementioned U.S. Patent Application Publication 2007/0100348 or the fixation delivery apparatus illustrated in FIGS. 76A-76B and described in the corresponding text of commonly-assigned U.S. Patent Application Publication 2010/0094425. Each of the foregoing U.S. patent application publications is incorporated herein by reference in its entirety. Thus, the suture arrangement 90 is configured such that the tissue anchors 80, 85 can be slidably received in series in a tubular cannula of the delivery tool, with the tissue anchor 80 positioned within the tubular cannula distal to the tissue anchor 85 such that the tissue anchor 80 will be ejected first from the tubular cannula and into the soft tissue of the patient proximate the implantation site. As further described in the aforementioned U.S. patent application publications, the delivery tool can then be repositioned and the tubular cannula reinserted into the tissue at a different location with a portion of the suture loop 98 of the suture arrangement 90 spanning across and over the implantation site. When present, the safety line 120 is secured to the delivery tool and operates to prevent unintended ejection of the tissue anchor 85 during ejection of the tissue anchor 80 and repositioning of the delivery tool. Once both tissue anchors 80, 85 are inserted into the tissue, the suture loop 98 can be tightened by pulling on the tether 105 under resistance applied by engagement of the tissue anchors 80, 85 and the tissue. Excess lengths of the tether 105 and the safety line 120 can then be manually cut away or automatically cut by a feature in the delivery tool.

Figure 5A:
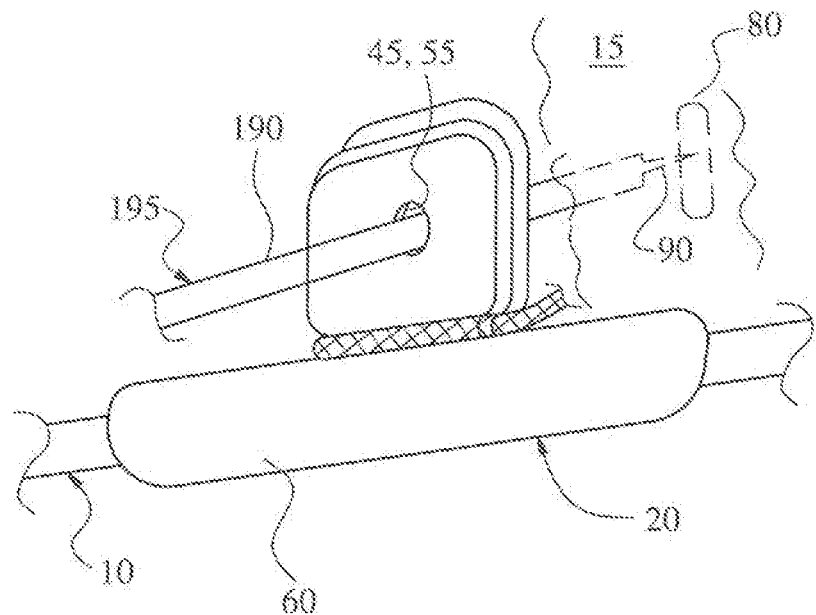
FIGS. 5A-5B through 7A-7B are perspective views and side views, respectively, of the medical implant and anchor element of FIG. 1 in stages of implantation using a fixation element and fixation element delivery tool according to one embodiment.
Figure 5B:
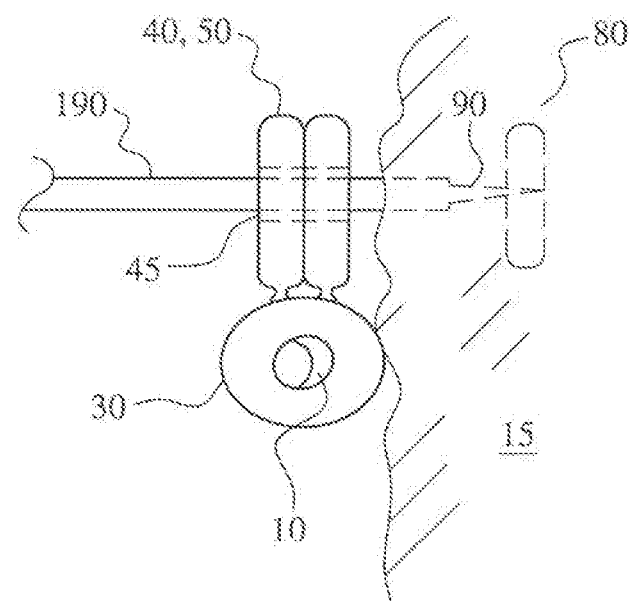

FIGS. 5A-5B through 7A-7B are perspective views and side views, respectively, of the medical implant 10 and anchor element 20 in progressive stages of implantation using the fixation element 25 and a fixation element delivery tool as 6 described above, according to one embodiment. As shown in FIGS. 5A-5B, with the suture loop 70 holding the anchor element 20 in its folded configuration and the implant 10 positioned within the intermediate portion 60 of the anchor element, the anchor element 20 and implant 10 are positioned as desired against or proximate the tissue 15 at the implantation site. As further shown, a cannula 190 of a fixation element delivery tool 195, which as explained previously, carries the fixation element 25, is inserted through the eyelets 45, 55 of the anchor element 20 and into the tissue 15. FIGS. 5A-5B also show the tissue anchor 80 of the fixation element 25 after it has been ejected from the cannula 190 into the tissue 15 so as to engage the tissue 15.

Figure 6A:
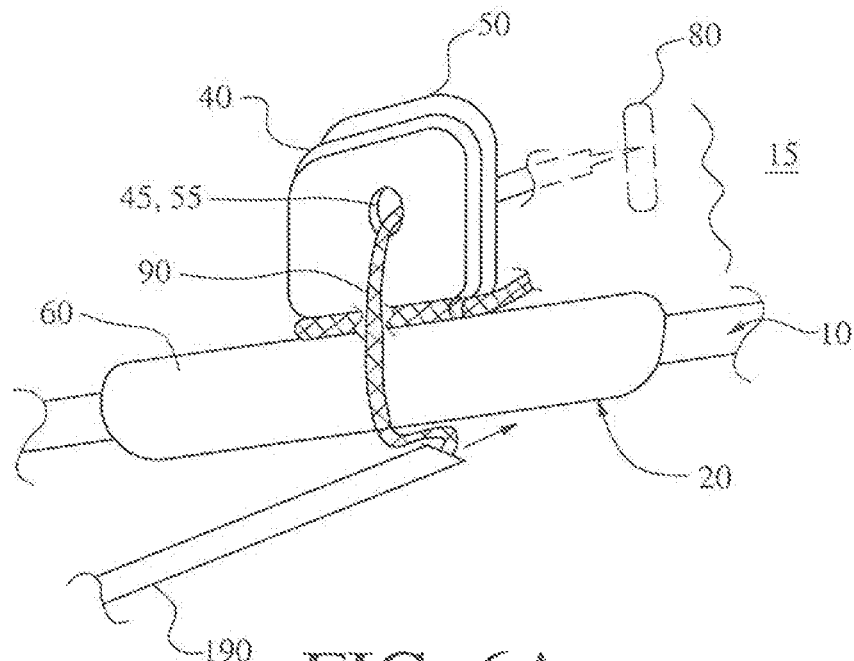
Figure 6B:
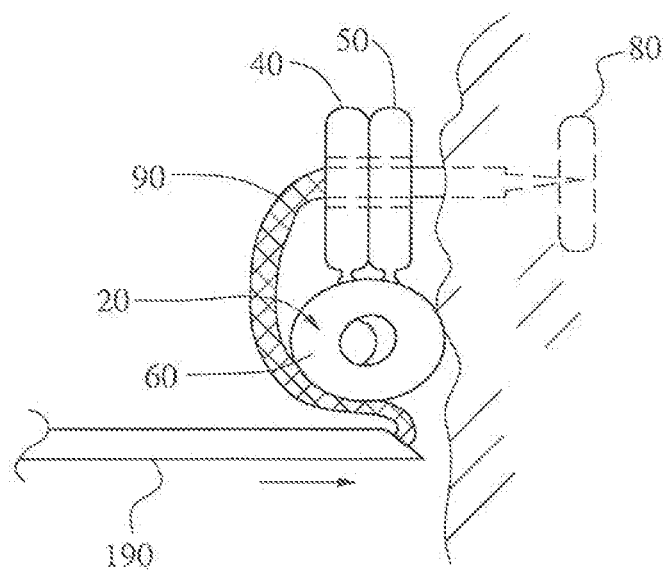

As shown in FIGS. 6A-6B, the cannula 190 is then withdrawn from the tissue 15 and the eyelets 45,55, and then repositioned to the side of the anchor element 20 such that a portion of the adjustable suture arrangement 90 spans over and across the intermediate portion 60 of the anchor element. As further shown, the cannula 190 can then be reinserted into the tissue 15 proximate the anchor element 20.

Figure 7A:
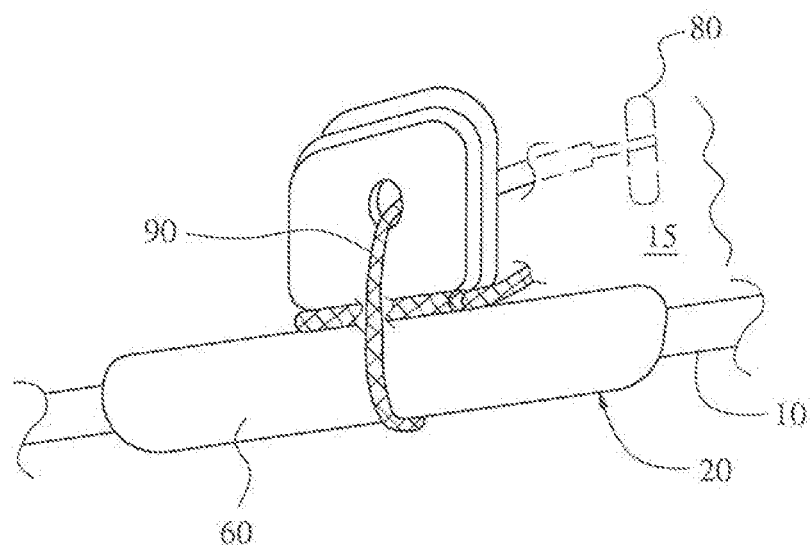
Figure 7B:
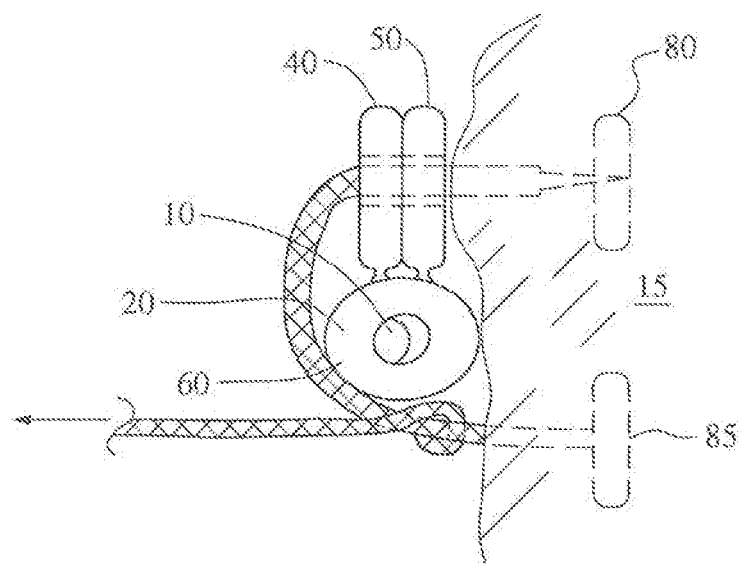

Next, as can be seen in FIGS. 7A-7B, after the tissue anchor 85 has been deployed into the tissue at the second insertion location, the cannula 190 can be withdrawn again and the tether 105 pulled to tighten the adjustable suture arrangement 90 with the engagement of the tissue anchors 80, 85 and the tissue 15 resisting the pulling force. In this manner, the portion of the adjustable suture arrangement 90 spanning across the intermediate portion 60 of the anchor element 20 compresses the intermediate portion 60 against the tissue, thus securing the anchor element 20 and the implant 10 in place. As discussed previously, any excess length of the suture arrangement 90 can then be cut away.

Figure 8:
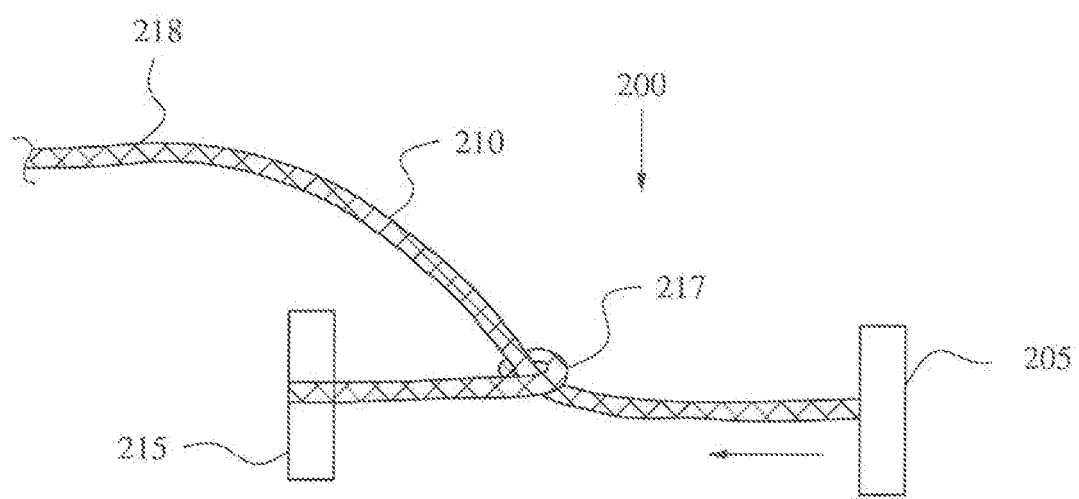
FIG. 8 is a schematic illustration of an alternative fixation element for use in securing the medical implant and anchor element of FIG. 1 to tissue according to another embodiment.

FIG. 8 is a schematic illustration of an alternative fixation element 200 for use in securing the medical implant 10 and the anchor element 20 of FIG. 1 to tissue according to another embodiment. As shown, the fixation element 200 includes a tissue anchor 205, a suture arrangement 210 and a pledget 215. The tissue anchor 205 is fixedly connected to one end of the suture arrangement 210, and the pledget 215 is fixedly connected to an opposite end of the suture arrangement 210, with a slip knot 217 disposed in the suture arrangement 210 between the tissue anchor 205 and the pledget 215, and a tether 218 extends from the slip knot 217 in a proximal direction. 7 The suture arrangement 210 is configured such that pulling on the tether 218 causes the tissue anchor 205 to be drawn toward the pledget to place the suture arrangement 210 between the pledget 215 and the tissue anchor 205 in tension. In general, the suture arrangement 200 can be configured and used in substantially the same or an identical manner as the fixation elements illustrated in FIGS. 13-14 and described in the corresponding text of commonly-assigned U.S. Patent Application Publication 2007/0100348, which is incorporated herein by reference in its entirety.

In various embodiments, the fixation element 200 can be delivered using a fixation element delivery tool such as, for example, the delivery device 400 illustrated in FIGS. 13-15 and 20-21 and described in the corresponding text of commonly-assigned U.S. Patent Application Publication 2007/0100348, which is incorporated herein by reference in its entirety. As described in the aforementioned U.S. patent publication, the delivery tool for the fixation element 200 includes a tubular cannula configured to receive the tissue anchor 205 during insertion in to the tissue at the implantation site, and upon withdrawal of the tubular cannula from the tissue, to cause the suture arrangement 210 between the tissue anchor 205 and the pledget 215 to be placed in tension under resistance supplied by engagement of the tissue by the tissue anchor 205.

Figure 9A:
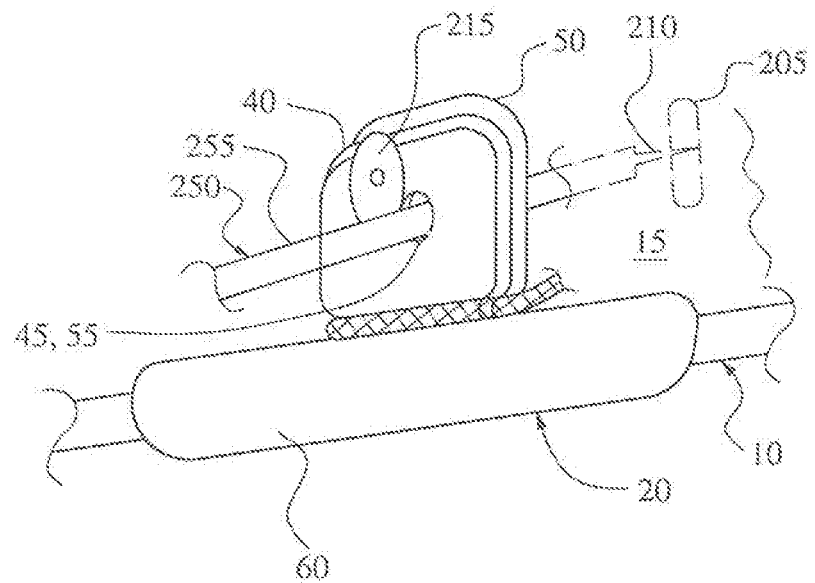
FIGS. 9A-9B and 10A-10B are perspective views and side views, respectively, of the medical implant and anchor element of FIG. 1 in stages of implantation using a fixation element and fixation element delivery tool according to another embodiment.
Figure 9B:
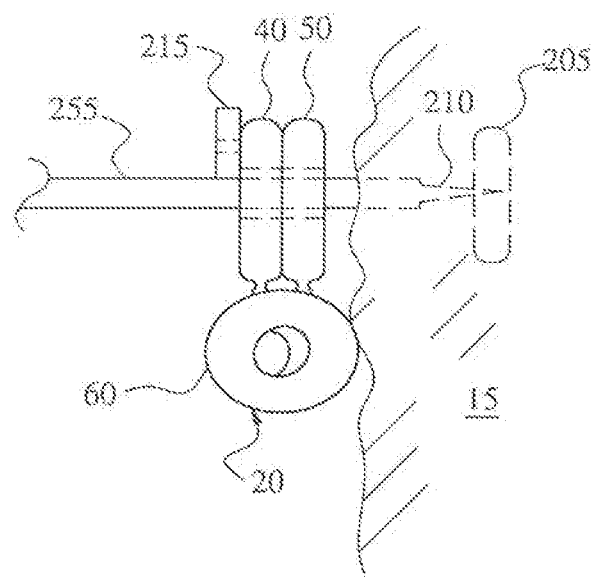

FIGS. 9A-9B and 10A-10B are perspective views and side views, respectively, of the medical implant 10 and anchor element 20 in stages of implantation using the fixation element 200 and a fixation element delivery tool 250 according to another embodiment. As shown in FIGS. 9A and 9B, with the suture loop 70 holding the anchor element 20 in its folded configuration and the implant 10 positioned within the intermediate portion 60 of the anchor element, the anchor element 20 and implant 10 are positioned as desired against or proximate the tissue 15 at the implantation site. As further shown, the fixation element delivery tool 250, which as explained previously, carries the fixation element 200, includes a cannula 255 that is inserted through the eyelets 45, 55 of the anchor element 20 and into the tissue 15. FIGS. 9A-9B also show the tissue anchor 205 of the fixation element 200 after it has been ejected from the cannula 255 into the tissue 15 so as to engage the tissue 15. As further shown, with the 8 cannula 255 inserted the desired distance into the tissue 15, the pledget 215 of the fixation element 200 bears against the tab 40 of the anchor element 20.

Figure 10A:
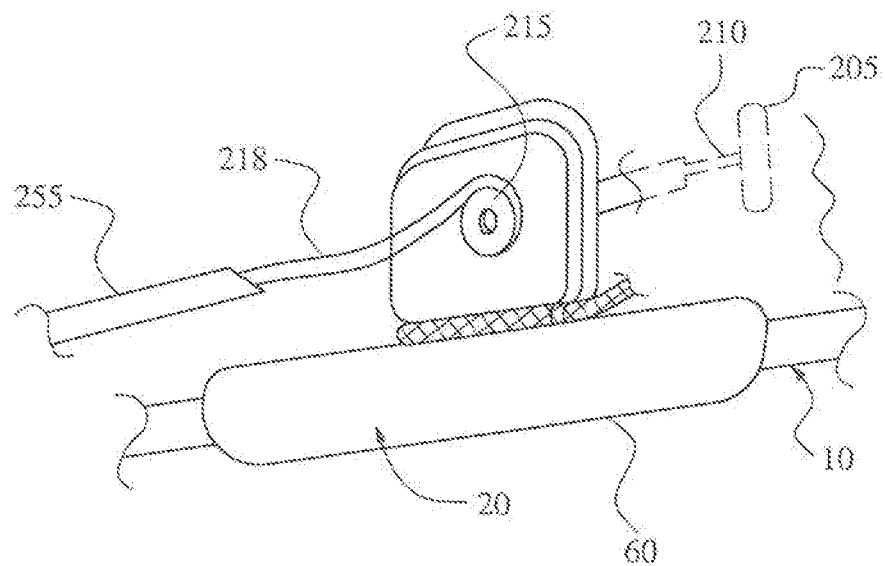
Figure 10B:
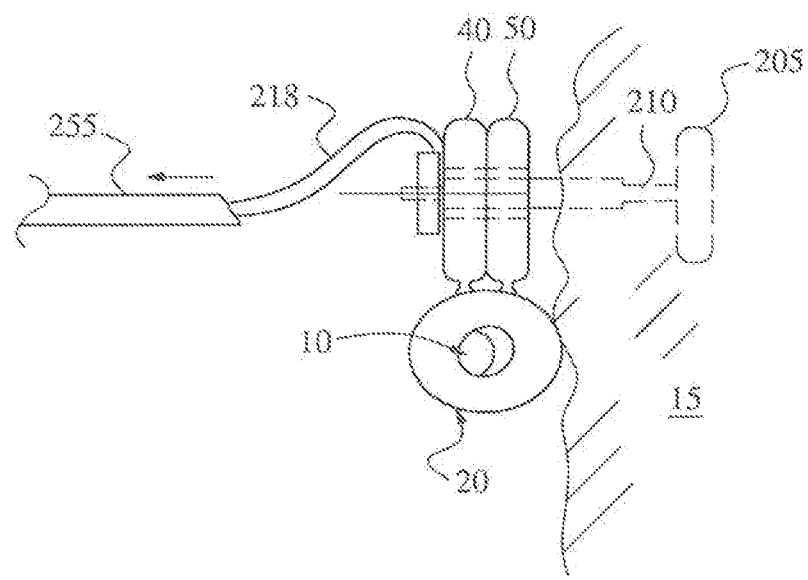

As can be seen in FIGS. 10A-10B, the cannula 255 is then withdrawn from the tissue 15 and from the eyelets 45, 55 of the anchor element 20, which in turns pulls on the tether 218 thus tending to pull together the tissue anchor 205 and the pledget 215. Because, as shown in FIGS. 10A-10B, the pledget 215 bears against the tab 40 and the tissue anchor 205 is embedded in and in engagement with the tissue 15, this pulling action tends to compress the tabs 40, 50 of the anchor element against the tissue 15 thus securing the anchor element 20 and the implant 10 in place. Here again, any excess length of the suture arrangement of the fixation element 200 can then be cut away.

As discussed previously, the fixation elements 25, 200 and the methods discussed herein can be used in connection with any implants and anchor elements of similar structure to the anchor element 20, e.g., including eyelets or similar features for receiving sutures and tissue anchors such as those utilized in the fixation elements 25, 200.

In addition, in the illustrated embodiments, only a single fixation element 25, 200 is illustrated and described. In various embodiments, however, additional fixation elements 25, 200 can be used in combination. For example, in one embodiment, two fixation elements 25 can be utilized, one being deployed as described above, and another being deployed across the intermediate portion 60 or the tabs 40, 50 to provide additional fixation to the tissue 15. In another embodiment, a fixation element 200 can be deployed as described above, and a fixation element 25 can also be deployed with a tissue anchor 80, 85 on either side of the intermediate portion 60 of the anchor element 20. Additional combinations of fixation elements 25, 200 will be readily apparent to those skilled in the art based on the foregoing.

Figure 11A:
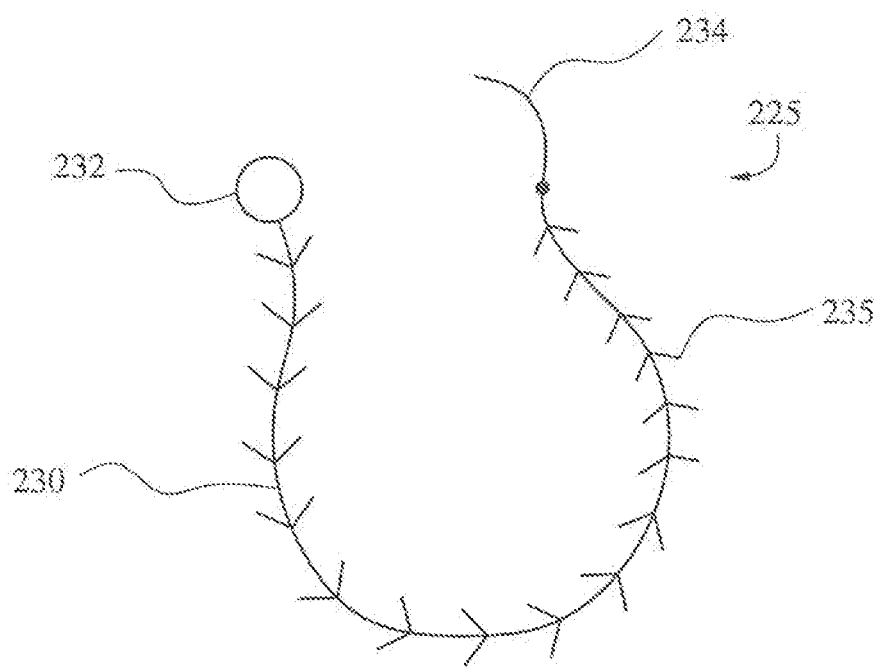
FIG. 11A is a schematic view of an alternative fixation element.
Figure 11B:
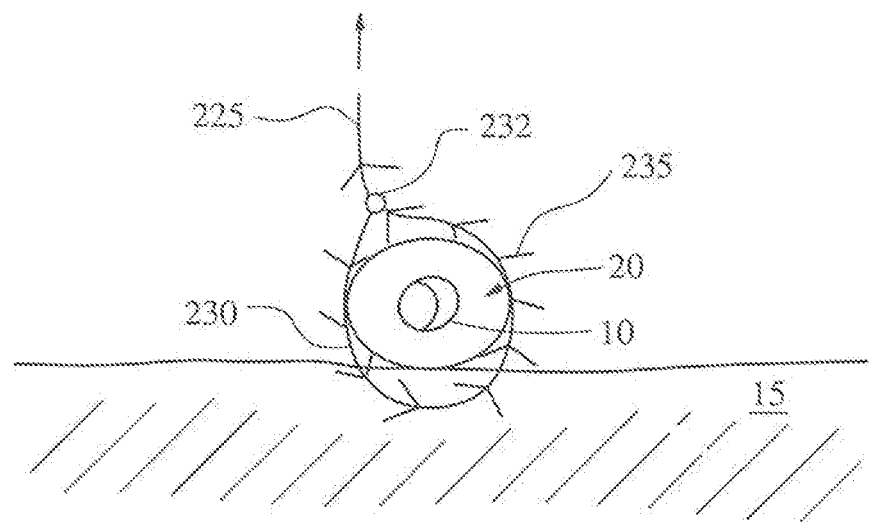
FIG. 11B illustrates the alternative fixation element of FIG. 11A in use in an alternative technique for anchoring the medical implant and anchor element of FIG. 1 to tissue, according to another embodiment of the present invention.

FIG. 11A is a schematic view of an alternative fixation element 225, and FIG. 11B is a schematic end view illustrating the fixation element 225 in use in an alternative technique for anchoring an implant, such as the implant 10, to soft tissue 15. As shown, the implant 10 with the anchor element 20 coupled thereto can be sutured to the soft tissue 15 using the alternative fixation element 225, which in the illustrated 9 embodiment is in the form of a barbed suture. As shown, the barbed suture fixation element 225 includes a main body 230 having an eyelet 232 at its proximal end, and a plurality of barbs 235 projecting laterally from the main body 230 along the length thereof. As shown in FIG. 11A, a curved needle 234 is connected to the body 230 at its distal end, and this facilitates deploying the fixation element 225 in a conventional manner such as is typically used for suturing tissue. As further shown, the distal end of the body 230 can be routed through the eyelet 232 to form a suture loop extending around the anchor element 20 of the implant 10. The barbs 235 are oriented so as to allow the body 230 to be routed through the eyelet 232, but because they extend laterally relative to the body 230, to prevent subsequent withdrawal of the body 230 through the eyelet 232 in the opposite direction. The cooperation of the eyelet 232 and the barbs 235 thus form a locking arrangement to secure the fixation element 225 under tension, thereby securing the implant 10 to the tissue 15. This arrangement thus eliminates the need for a separate knot to facilitate tightening the suture. In addition, the orientation of the barbs 235 further provides minimal resistance to forward advancement of the fixation element 225 into the tissue 15, while at the same time resisting movement of the fixation element 225 in the reverse direction.

In various embodiments, the barbed fixation element 225 can be manually deployed in a conventional manner, e.g., using a suture needle and a manual suturing technique as is known in the art. In various embodiments, the barbed fixation element 225 can be coupled to one or more tissue anchors and pre-loaded onto a fixation element delivery tool such as, for example, the fixation delivery apparatus illustrated in FIGS. 33A-33D of the aforementioned U.S. Patent Application Publication 2007/0100348 or the fixation delivery apparatus illustrated in FIGS. 76A-76B and described in the corresponding text of commonly-assigned U.S. Patent Application Publication 2010/0094425.

The barbed fixation element 225 can be formed from a variety of biocompatible materials, including materials conventionally used in suture manufacture. Exemplary materials include, without limitation, polymers made of polyglycolic acid, poly-tri-methylene-carbonate, poly-1,4-dioxane-2-one, poly-caprolactone, p-dioxanone, nylon 6, and isotactic polypropylene. However, it is emphasized that the particular 10 materials used for manufacturing the barbed fixation element 225 is not limited to any particular material.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed as new and desired to be protected by Letters Patent of the United States:

1. A method of securing a catheter or electrode lead within a patient, the method comprising:
   providing a delivery tool comprising a distal tip, a tubular cannula extending to the distal tip, at least one tissue anchor slidably received within the tubular cannula, and an adjustable suture arrangement coupled to the at least one tissue anchor;
   inserting the distal tip of the delivery tool into soft tissue of the patient;
   ejecting the at least one tissue anchor from the delivery tool and into the soft tissue of the patient;
   withdrawing the delivery tool from the soft tissue while leaving the at least one tissue anchor in the soft tissue of the patient;
   disposing a portion of a catheter or electrode lead between the adjustable suture arrangement and the soft tissue; and
   tightening the adjustable suture arrangement to secure the portion of the catheter or electrode lead against the soft tissue.

2. The method of claim 1, further comprising positioning an anchor at a desired implantation position proximate the soft tissue of the patient, wherein the portion of the catheter or electrode lead is disposed within the anchor.

3. The method of claim 2, wherein inserting the distal tip of the delivery tool comprises inserting the distal tip of the delivery tool through a portion of the anchor and into the soft tissue.

4. The method of claim 3, wherein the anchor comprises at least one tab.

5. The method of claim 4, wherein at least one of the least one tab comprises an eyelet.

6. The method of claim 5, wherein inserting the distal tip of the delivery tool comprises inserting the distal tip of the delivery tool through the eyelet of one of the at least one tab.

7. The method of claim 4, wherein the at least one tab is a plurality of tabs.

8. The method of claim 7, wherein each of the tabs comprises an eyelet.

9. The method of claim 2, further comprising disposing a suture loop around the anchor to retain the anchor.

10. The method of claim 1, wherein the at least one tissue anchor comprises a pair of tissue anchors slidably received in the tubular cannula of the delivery tool and coupled to the adjustable suture arrangement.

11. The method of claim 10, wherein ejecting the at least one tissue anchor comprises ejecting one of the tissue anchors from the delivery tool and into the soft tissue prior to withdrawing the delivery tool from the soft tissue, and subsequently re-inserting the delivery tool into the soft tissue at a different location such that a portion of the adjustable suture arrangement between the tissue anchors spans over the portion of the catheter or electrode lead, ejecting another one of the tissue anchors into the soft tissue, and withdrawing the delivery tool from the soft tissue after ejecting the other one of the tissue anchors.

12. The method of claim 10, wherein tightening the adjustable suture arrangement comprises tightening a portion of the adjustable suture arrangement between the pair of tissue anchors to secure the portion of the catheter or electrode lead spanned by the adjustable suture arrangement to the soft tissue.

13. The method of claim 10, further comprising inserting each of a second pair of tissue anchors into the soft tissue on opposite sides of the catheter or electrode lead with a second adjustable suture arrangement coupled to the second pair of tissue anchors and extending across the catheter or electrode lead and tightening the second adjustable suture arrangement against the catheter or electrode lead.

14. The method of claim 1, wherein the catheter or electrode lead is a drug delivery catheter.

15. The method of claim 1, wherein the catheter or electrode lead is the electrode lead.

16. The method of claim 15, wherein the electrode lead is configured and arranged for use in deep brain stimulation.

17. The method of claim 15, further comprising coupling the electrode lead to a stimulator.

18. The method of claim 1, wherein the adjustable suture arrangement comprises at least one knot configured to permit tightening of the adjustable suture arrangement and to resist subsequent loosening thereof.

19. The method of claim 1, wherein each of the at least one tissue anchor comprises at least one passage extending through the at least one tissue anchor with a portion of the adjustable suture arrangement extending through the at least one passage.

20. The method of claim 1, wherein each of the at least one tissue anchor comprises at a plurality of passages extending through the at least one tissue anchor with a portion of the adjustable suture arrangement extending through each of the plurality of passages.

* * * * *